United States Patent [19]

Augustine

[11] Patent Number: 5,235,970
[45] Date of Patent: Aug. 17, 1993

[54] TRACHEAL INTUBATION WITH A STYLET GUIDE

[75] Inventor: Scott D. Augustine, Bloomington, Minn.

[73] Assignee: Augustine Medical, Inc., Eden Prairie, Minn.

[21] Appl. No.: 902,777

[22] Filed: Jun. 23, 1992

Related U.S. Application Data

[63] Continuation of Ser. No. 499,057, Mar. 26, 1990, abandoned.

[51] Int. Cl.$^5$ .......................................... A61M 16/00
[52] U.S. Cl. ........................... 128/200.26; 128/207.14
[58] Field of Search ............... 128/200.26, 207.14, 128/207.15; 604/95

[56] References Cited

U.S. PATENT DOCUMENTS

| | | | |
|---|---|---|---|
| 2,541,402 | 2/1951 | Caine | 128/200.26 |
| 2,855,934 | 10/1958 | Daughaday, Jr. | 604/95 |
| 2,862,498 | 12/1958 | Weekes | 128/207.14 |
| 3,503,385 | 3/1970 | Stevens | 604/95 |
| 3,538,918 | 11/1970 | Engelsher | 128/200.26 |
| 3,802,440 | 4/1974 | Salem et al. | 128/200.26 |
| 3,957,055 | 5/1976 | Linder et al. | 128/200.26 |
| 4,069,820 | 1/1978 | Berman | 128/200.26 |
| 4,244,362 | 1/1981 | Anderson | 128/207.14 |
| 4,529,400 | 7/1985 | Scholten | 128/207.14 |
| 4,533,540 | 11/1985 | Straith | 128/200.26 |
| 4,612,927 | 9/1986 | Krüger | 128/200.26 |
| 4,662,870 | 5/1987 | Augustine et al. | 604/117 |
| 4,685,457 | 8/1987 | Donenfeld | 604/95 |
| 4,819,619 | 4/1989 | Augustine et al. | 128/200.26 |
| 4,832,020 | 5/1989 | Augustine | 128/207.14 |
| 4,840,172 | 6/1989 | Augustine et al. | 128/207.14 |
| 4,892,095 | 1/1990 | Nakhgerary | 128/200.26 |
| 4,925,445 | 5/1990 | Sakamoto et al. | 604/95 |
| 5,058,577 | 10/1991 | Six | 128/200.26 |

FOREIGN PATENT DOCUMENTS 0284335 3/1988 European Pat. Off. .

OTHER PUBLICATIONS

British Journal of Anaesthesia, "A New Blade for Blind Endotracheal Intubation", J. B. & S. R. Liban, pp. 1279-1280.

*Primary Examiner*—Edgar S. Burr
*Assistant Examiner*—Aaron J. Lewis
*Attorney, Agent, or Firm*—Baker, Maxham, Jester & Meador

[57] ABSTRACT

An endotracheal stylet guide includes an elongate, arcuate section, and a substantially J-shaped tracheal-seeking section on the distal end of the arcuate section. The stylet guide is inserted, distal end first, into an endotracheal tube. The tube is positioned in the throat such that the J-shaped, tracheal-seeking section is adjacent the epiglottis, opposing the opening to the larynx. The stylet guide is advanced in the endotracheal tube, and the J-shaped section enters and tracks down the trachea. The endotracheal tube is then advanced on the stylet guide, into the trachea. The stylet guide is removed and intubation then proceeds conventionally.

11 Claims, 4 Drawing Sheets

5,235,970

TRACHEAL INTUBATION WITH A STYLET GUIDE

This is a continuation of application Ser. No. 07/499,057, filed Mar. 26, 1990, now abandoned.

BACKGROUND OF THE INVENTION

This invention relates to a stylet guide insertable in an endotracheal tube which is used to guide the endotracheal tube into the trachea (windpipe) of a patient.

As taught in my U.S. Pat. No. 4,832,020, endotracheal intubation is greatly assisted by my tracheal intubation guide which includes a tubular member having a curved forward end shaped to follow the curvature of the back of the tongue and anterior surface of the throat of a patient and a rear end for projecting out through the mouth of the patient. An anterior guide surface beneath the tubular member guides the member into the throat of a patient. The guide surface has a forward indent for engaging the front of the epiglottis and for seating over the hyo-epiglottic ligament. When seated, the tubular member is positioned opposite the opening to the larynx, and an endotracheal tube previously inserted into the tubular member can be advanced through the guide into the trachea. My tracheal intubation guide has met with wide acceptance and in most applications works as intended.

In order to guide the tube into the larynx, a sharp anterior bend must be imposed on the end of the tube to orient the end toward the epiglottus. This bend is imposed by the configuration at the end of my intubation guide. However, the very short distance between the larynx and the end of the intubation guide prevents the end of the tube being pointed downwardly in the trachea. Instead, it must be turned downwardly by contacting the anterior surface of the larynx. Occasionally, the edge at the end of the anteriorly directed tube will catch on surface irregularities of the larynx, preventing advancement into the trachea.

Yet, the curvature imposed on the end of the tube must be maintained in order to ensure proper entrance of the tube into the larynx, and to avoid incorrect insertion into the esophagus.

SUMMARY OF THE INVENTION

This invention provides a stylet guide made of a shape-retaining, flexible material which has, at its distal end, a tracheal-seeking offset. When the stylet guide is inserted into an endotracheal tube and the tube is placed in my tracheal intubation guide and the guide is seated on the hyo-epiglottic ligament, the tracheal-seeking offset extends toward the posterior surface of the epiglottis. When the stylet guide is advanced in the endotracheal tube, the tracheal-seeking offset tracks down the anterior surface of the larynx past the vocal cords and into the trachea. After the distal end of the stylet guide is advanced into the trachea, the endotracheal tube is advanced in the intubation guide, being guided by the stylet past the epiglottis and into the trachea. The tube is tracked into the larynx by the stylet guide. Therefore, the intubation guide no longer needs to impose the sharp anterior bend on the end of the tube. Resultantly, correct placement of the tube is virtually assured on the first attempt.

The stylet guide has a central passageway extending from its proximal to its distal end and openings that penetrate from the surface to the central passageway at the tracheal offset. This permits the practitioner to distinguish placement in the trachea from accidental placement in the esophagus. When a syringe is connected to the proximal end of the stylet guide, no resistance will be encountered in withdrawing the plunger from the syringe when the distal end of the stylet guide is in the air passageway. However, if accidentally seated in the esophagus, the distal end will be sandwiched in the closed ovoid of the esophagus in such a manner as to prevent air passing into the holes. The practitioner then will draw a vacuum through the syringe, indicating placement in the esophagus.

It is, therefore, an objective of this invention to provide a medical instrument which ensures accurate placement of an endotracheal tube in a trachea.

Another objective is to provide such an instrument with the ability to guide the endotracheal tube through the larynx, into the trachea, while avoiding the irregularities in the anterior surface of the larynx.

A distinctive advantage of this invention is that it permits the practitioner to distinguish tracheal from esophagal placement.

These and other objectives and advantages of this invention will become evident when the following description is read with reference to the below-described drawings.

DETAILED DESCRIPTION OF THE PREFERRED EMBODIMENT

Figure 1:
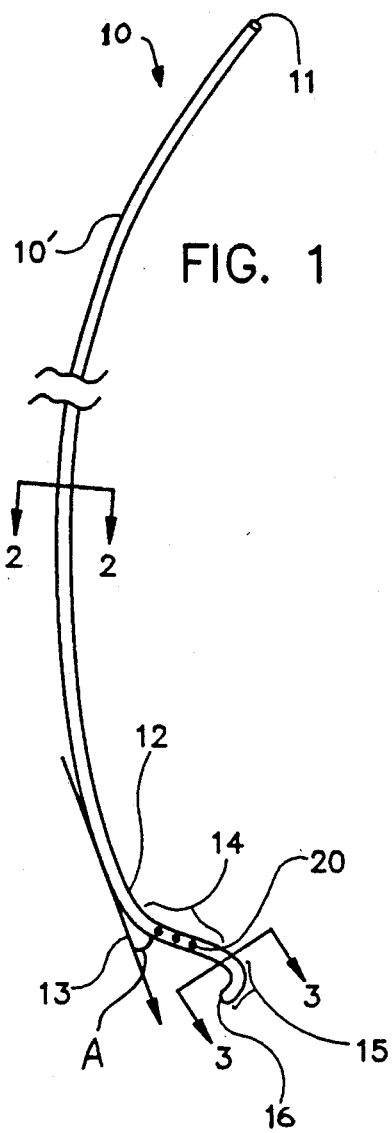
FIG. 1 is a side view of an endotracheal stylet guide according to the invention.
Figure 2:
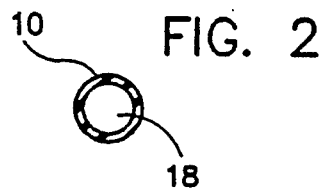
FIG. 2 is a cross-section of the stylet guide taken along line 2—2 of FIG. 1.
Figure 3:
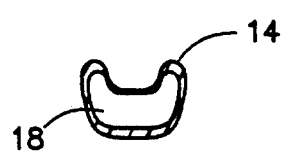
FIG. 3 is a cross-section of the tracheal offset at the distal end of the stylet guide taken along line 3—3 of FIG. 1.

FIGS. 1, 2, and 3 illustrate an endotracheal stylet guide 10 having proximal and distal ends 11 and 12, respectively, The stylet guide 10 has a generally arcuate front section 10' extending between the proximal and distal ends. At the distal end 12, the stylet transitions from its generally arcuate shape to an offset 14. The offset 14 is generally coplanar with the front section 10' of the stylet guide 10 and extends into a circle of which the arcuate section forms a part. The angle A at the transition between the distal end 12 and the offset 14 is relatively sharp, being greater than 20 degrees with respect to a tangent 13 touching the arcuate section at the distal end 12. The offset 14 is shorter than the front arcuate section 10' of the stylet. This offset transitions, in turn, to a second offset 15 which extends in the direction of the tangent 13. The offset 15 terminates in a rounded bulbous tip 16. The stylet guide 10 has a central passageway which extends from the proximal end 11 through the offset 14 to the rounded tip 16. The passageway is indicated by reference numeral 18 in FIGS.

2 and 3 which are, respectively, enlarged cross-sections of the stylet guide taken at 2—2 and 3—3 in FIG. 1.

A set of holes, one indicated by reference numeral 20, is provided in the offset 14. These holes extend through the offset to the central passageway 18.

The stylet guide of FIGS. 1, 2, and 3 is preferably formed from a relatively flexible, shape-retaining material. FIG. 1 illustrates the stylet guide in its non-flexed configuration. The stylet guide can be flexed in any of its portions from the unflexed configuration of FIG. 1, and will resume the configuration of FIG. 1 when the flexing pressure is removed. Preferably, the portion of the stylet guide 10 formed by the offset 15 is more flexible than the rest of the stylet guide 10 and may be formed on the end of the stylet using a soft rubber-like material.

The surface of the stylet guide 10 is entirely smooth and presents no sharp edges which can lacerate tissue.

Figure 4:
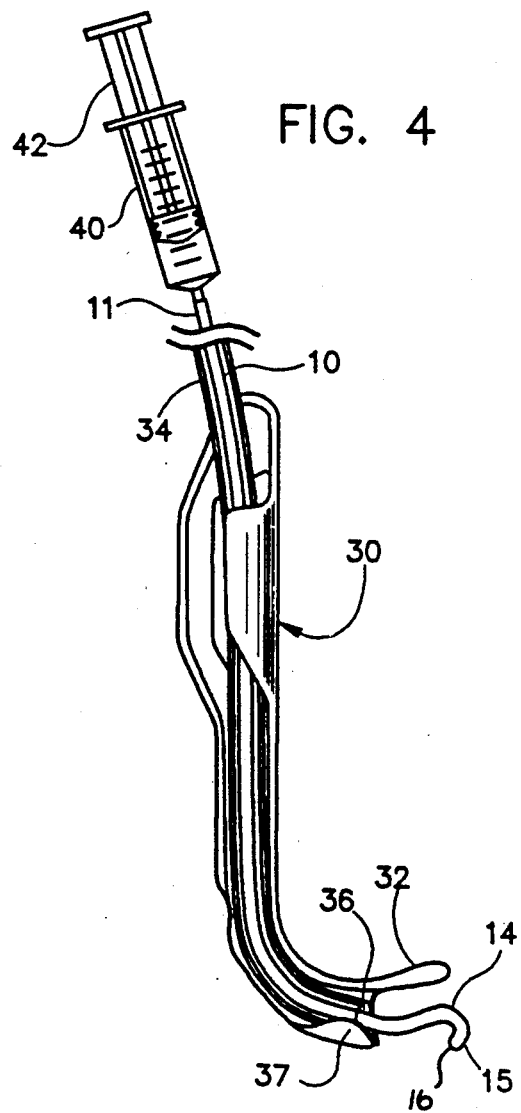
FIG. 4 is a side view, in partial cross-section showing the stylet guide of FIG. 1 inserted into an endotracheal tube which has been inserted in my tracheal intubation guide.

Refer now to FIG. 4 for an understanding of how the stylet guide 10 of FIG. 1 is used in combination with my tracheal intubation guide. For a complete understanding of my tracheal intubation guide, reference is made to U.S. Pat. No. 4,832,020, which is incorporated herein by reference in its entirety. The intubation guide 30 includes a forward end 32 with an indent for engaging the hyo-epoglatic ligament. An endotracheal tube 34 having a distal tip 36 is advanced in my tracheal intubation guide 30 until its tip 36 abuts the forward retention flange 37. The stylet guide 10 is fed, distal tip first, into the endotracheal tube 34 until the offset 15 extends out of the distal tip 36 of the endotracheal tube, beyond the retention flange 37 of the tracheal intubation guide. FIG. 4 also shows a syringe 40 connected conventionally to the proximal end 11 of the stylet guide 10. The syringe 40 has a plunger 42. With the arrangement of FIG. 4, movement of the plunger 42 in the syringe 40 will be unimpeded. Air will be displaced in response to movement of the plunger 42 through the central passageway 18 and the offset holes 20 of the stylet guide 10.

Refer now to FIGS. 1 and 4 for an understanding of how the stylet guide 10 operates. The arcuate front section of the stylet guide 10 conforms approximately to the curved anatomy of the throat. Assuming that the stylet guide 10 is conformed to the curvature of the back of the throat by the arrangement illustrated in FIG. 4, one will appreciate that the combination of the arc in the arcuate section and the offset 14 provides a sharp anterior curve in the direction of the end 32 of the intubation guide 30. When the end 32 is seated on the hyo-epoglatic ligament, the offset 14 extends toward the epiglottis. Sliding the stylet guide 10 forwardly in the endotracheal tube 34 will advance the offset 14 in the direction of the anterior surface of the larynx toward the vocal cords. In this regard, the offset 14 "seeks" the trachea. Hence, the offset 14 is referred to as a "tracheal" or "tracheal-seeking" offset.

From another aspect, the offsets 14 and 15 form a J-shaped, or hook-shaped, tracheal offset at the distal end of the arcuate section.

Figure 5:
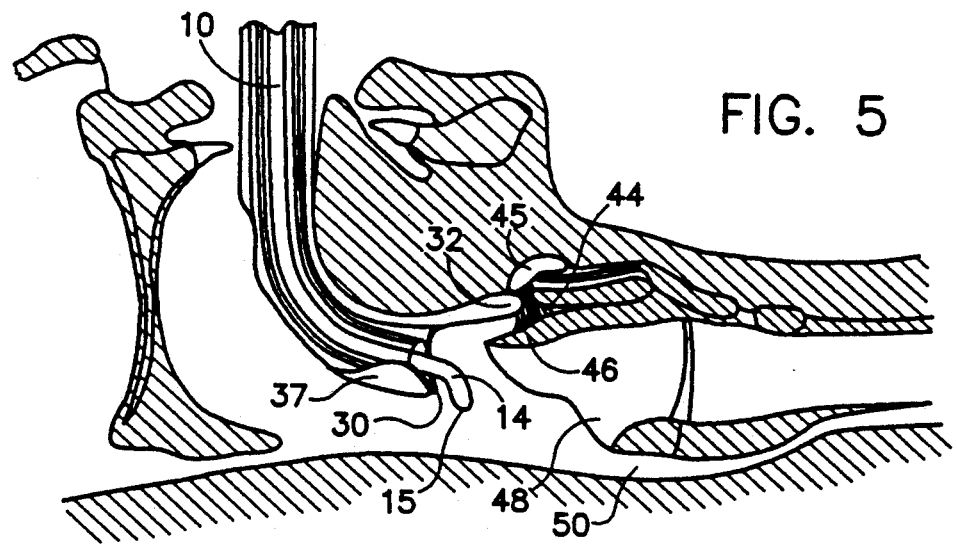
FIGS. 5, 6, 7, 8, 9, and 10 illustrate how the stylet guide reliably locates the trachea, tracks down the anterior surface of the esophagus, and provides a guide to accurately position the endotracheal tube in the trachea.
Figure 6:
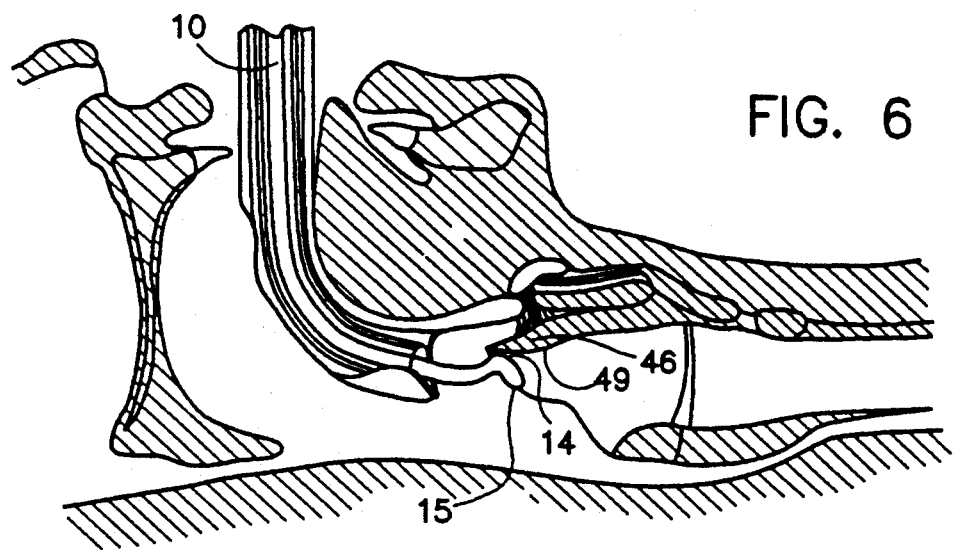

The operation of the combination illustrated in FIG. 4 in patient intubation is illustrated in FIGS. 5–10. In FIG. 5, the intubation guide 30, endotracheal tube 34, and stylet guide 10 arranged as illustrated in FIG. 4 are inserted into the throat and over the back of the tongue of a patient. As described in the incorporated patent, the end 32 of the guide engages the hyo-epiglottic ligament 44 and seats between the hyoid bone 45 and the epiglottus 46. This aligns the distal end 36 of the endotracheal tube with the opening of the larynx 48. In this regard, the back of the "J" shape is oriented toward the epiglottus and the anterior surface of the larynx. As illustrated in FIG. 5, the stylet guide is oriented so that tracheal offset 14 is also aligned with the larynx 48. In FIG. 6, the stylet guide 10 is advanced forwardly in the tube 34 so that the tracheal offset 14 is pushed toward and engages the anterior surface 49 of the larynx. As FIG. 6 emphasizes, the sharp angle of the tracheal offset 14 causes this end of the stylet guide 10 to "seek" the trachea.

Figure 7:
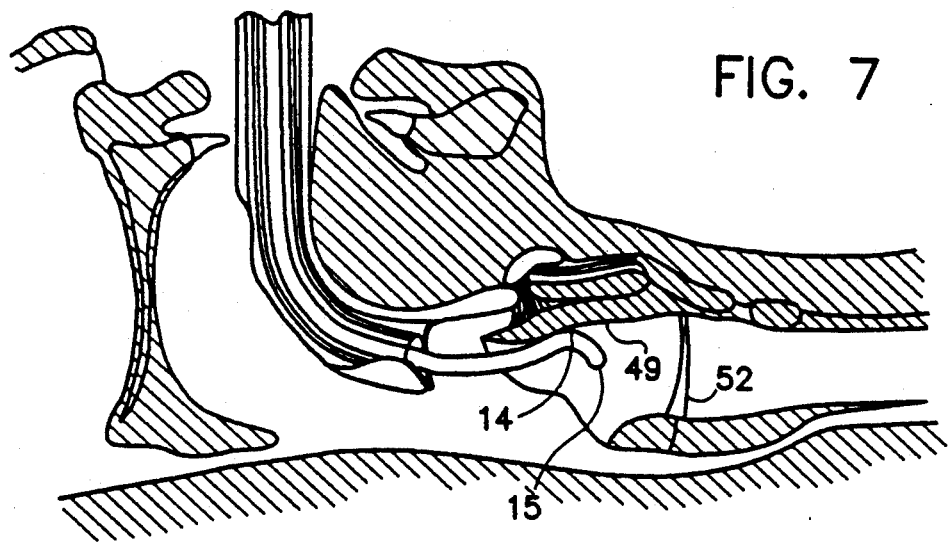
Figure 8:
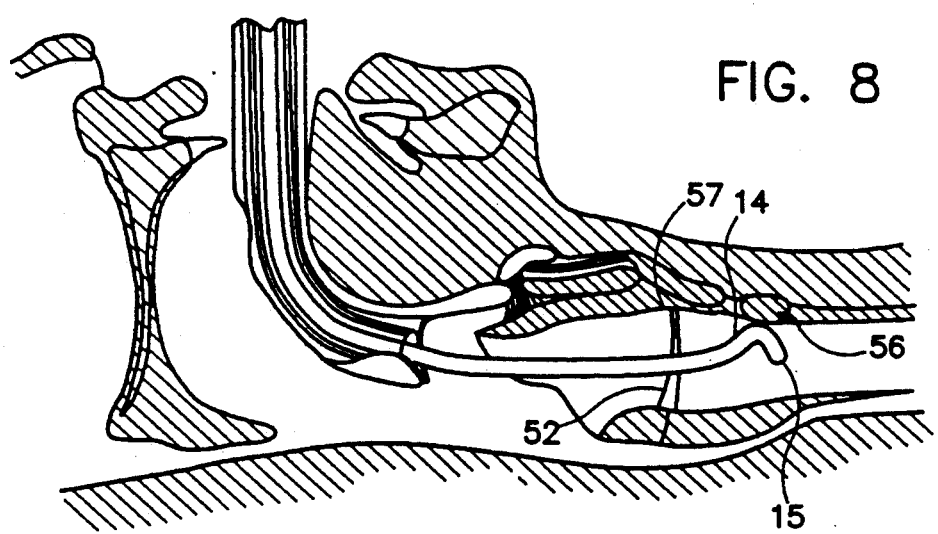

In FIG. 7, the stylet guide 10 has been advanced further into the endotracheal tube 34. As the stylet is advanced, the generally "J"-configuration of the offsets 14 and 15 causes the end of the stylet to maintain contact with the anterior surface of the epiglottus and track downwardly in the trachea toward the vocal cords 52. Since this portion of the stylet is more flexible than the rest, with a smooth anterior surface it will tend to easily track along the anterior envelope of the trachea. This is important because, as FIGS. 7 and 8 show, the contour of the anterior surface of the trachea is uneven and is reinforced in its upper portion with cricoid cartilage 56. The soft, flexible material forming the offset 15 will traverse the uneven anterior contour of the trachea without catching on the irregularities of the larynx surface. Without the "tracking" offset 15, to smooth and soften the portion of the stylet guide 10 which contacts the interior of the trachea, the stylet might catch at the anterior comisure of the vocal cords 57 or against the cricoid cartilage or tracheal cartilages which support the trachea.

Figure 9:
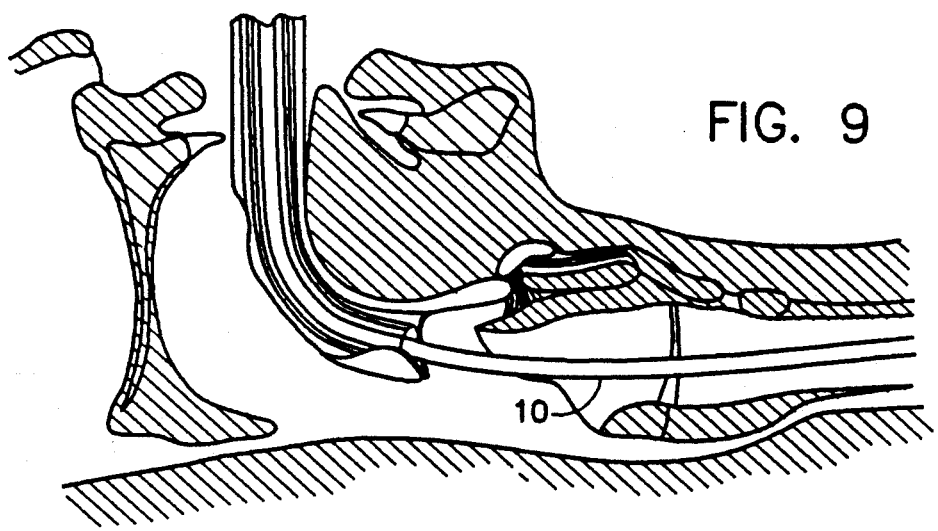
Figure 10:
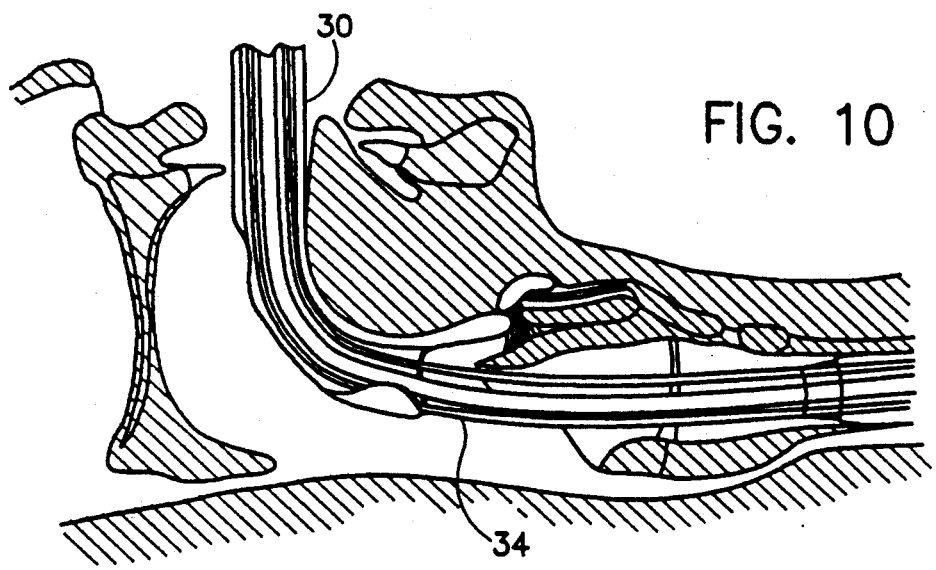

In FIG. 9, enough of the stylet guide 10 has been fed through the tube 34 to advance the distal end well past the vocal cords 52 toward the carina (not shown). As FIG. 9 shows, the offset 14 is still oriented anteriorly in the larynx, which, together with the curvature of the arcuate section positions the arcuate portion of the stylet guide 10 toward the posterior surface of the trachea. Now, as the endotracheal tube 34 is advanced along the stylet guide 10, the tip of the tube is guided reliably into the larynx, but is kept away from the anterior surface of the larynx and trachea, thereby reducing the risk of catching on surface irregularities. FIG. 10 illustrates the tube 34 being advanced well past the vocal cords toward the carina. After the tube 34 has been inserted substantially into the trachea, the stylet guide 10 is withdrawn, the tracheal intubation guide 30 is disengaged from the tube 34 and unseated from the hyo-epiglottic ligament and withdrawn from the mouth, keeping the tube in place in the trachea. The tube 34 is then seated.

Figure 11:
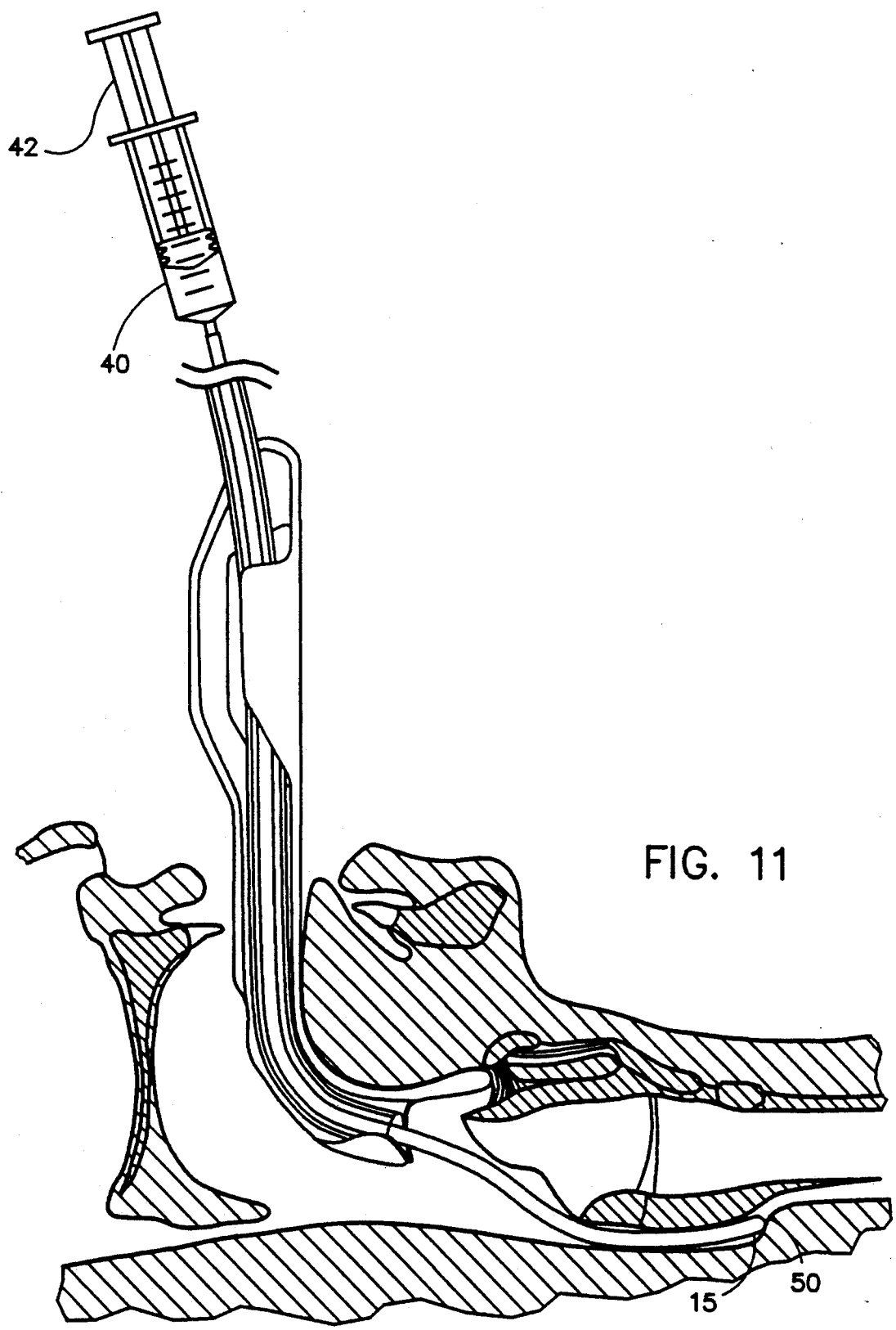
FIG. 11 illustrates detection of stylet placement in the esophagus.

FIG. 11 illustrates the use of the holes 20 in the tracheal offset 14 of the stylet. In FIG. 11, the stylet guide 10 has been erroneously fed into the esophagus 50. As is known, the esophagus is an oval-shaped channel, made of muscle and normally kept closed by compression between the trachea and the vertebral column. This configuration will tend to turn the J-shaped tip of the stylet guide 10 transversely so that the tracheal ofset 14 is substantially laterally oriented in the larynx (perpendicular to the plane of FIG. 11). In this position, the holes 20 will be oriented toward the flattened front and back of the esophagus. Incorrect seating can thus be detected by pulling the plunger 42 out of the syringe 40. The esophagus will contact and close the holes 20 and the practitioner will draw a vacuum in the syringe 40. The resistance of the vacuum is a clear signal that the tip of the stylet guide 10 has tracked into the esophagus.

Upon sensing the resistance to withdrawal of the plunger 42, the practitioner will retract the stylet guide and attempt once again to feed it into the trachea. The trachea is an open channel in which the tracking offset 14 will be oriented parallel to the plane of the drawings. This will keep the holes 20 in the tracheal offset open, with the result that the plunger 42 can be withdrawn without resistance from the syringe 40, thereby providing a clear indication that the stylet has been properly placed in the trachea.

While I have described several preferred embodiments of my endotracheal stylet guide, it should be understood that modifications and adaptations thereof will occur to persons skilled in the art. Therefore, the protection afforded my invention should only be limited in accordance with the scope of the following claims.

I claim:

1. A medical apparatus for guiding a tube into a trachea, comprising:
   an elongate, flexible member with a front section in the shape of an arc, the front section including distal and proximal ends;
   a flexible, tracheal-seeking offset on the distal end of the front section, the tracheal-seeking offset being substantially coplanar with and shorter than the front section, the tracheal-seeking offset forming an angle of greater than 20 degrees with a tangent to the arc at the distal end;
   a flexible tracking offset substantially coplanar with the front section and tracheal-seeking offset and extending toward the tangent;
   a central opening extending from the proximal end of the front section through the tracheal-seeking offset; and
   an opening in said tracheal-seeking offset, the opening extending from the surface of tracheal-seeking offset to the central opening.

2. The medical instrument of claim 1, wherein the openings extend out of a plane which intersects the front section, the tracheal-seeking offset, and the flexible tracking offset.

3. The medical apparatus of claim 1, wherein the tracheal-seeking and tracking offsets form a generally J-shaped section.

4. An apparatus for airway intubation, comprising:
   an endotracheal tube with proximal and distal ends;
   a tracheal intubation guide means for seating in the throat against the hyo-epiglottic ligament of a patient to retain and guide the endotracheal tube toward the trachea; and
   a stylet guide means for being slidably received in the endotracheal tube, the stylet guide means including an elongate flexible section having a generally arcuate shape, the flexible section having a distal end, and a tracheal-seeking means on the distal end for guiding the stylet guide means into the trachea;
   wherein the tracheal-seeking means includes a first offset on the distal end which is generally coplanar with an arc described by the elongate section, and a second offset on the first offset which is generally coplanar with the arc and the first offset.

5. The apparatus of claim 4, further including in the stylet guide means a central passageway extending from a proximal end of the elongate section into the tracheal-seeking means, and holes in the tracheal-seeking means extending from a surface of the tracheal-seeking means into the central passageway.

6. The apparatus of claim 4, wherein the first and second offsets form a generally J-shaped section.

7. The apparatus of claim 4, wherein the elongate section is formed from a flexible, shape-retaining material and the tracheal seeking means is formed from a flexible, shape retaining material.

8. The apparatus of claim 7, wherein the tracheal-seeking means is more flexible than the flexible section.

9. An endotracheal stylet guide, including:
   an arc-shaped flexible member with a proximal and a distal end;
   a substantially J-shaped, flexible tracheal-seeking offset on the flexible distal end;
   the tracheal-seeking offset being displaced from a tangent to the distal end by an angle of 20 degrees or greater; and
   a central passageway extending from the flexible member proximal end, through the flexible member, to the trachea-seeking offset, and an aperture in the tracheal-seeking offset opening from a surface of the tracheal-seeking offset into the central passageway.

10. A method for intubating the trachea of a patient using a stylet guide with an arcuate section having proximal and distal ends and a substantially J-shaped, tracheal-seeking offset on the distal end, wherein the elongate, flexible member is a flexible shape-retaining member and the generally J-shaped section is a flexible shape-retaining section, the method comprising the steps of:
   (a) inserting the stylet guide, tracheal-seeking offset first, into an endotracheal tube;
   (b) positioning the endotracheal tube in the throat of a patient such that a distal end of the endotracheal tube and the tracheal-seeking offset are adjacent the posterior surface of the epiglottus, opposing the opening to the larynx;
   (c) advancing the stylet guide through the distal end of the endotracheal tube so that the tracheal-seeking offset enters and tracks down the larynx and trachea;
   (d) advancing the endotracheal tube along the stylet guide into the larynx and trachea; and
   (e) withdrawing the stylet guide from the endotracheal tube while having the endotracheal tube in the trachea.

11. The method of claim 10, wherein the stylet guide includes a passage-way from the proximal end to the tracheal-seeking offset and an aperture opening from the passageway to a surface of the tracheal-seeking offset, further including the steps of:
   (c1) drawing air through the passageway to the proximal end; and
   (c2) if step c1 results in a vacuum, repeating steps (a)-(c), otherwise
   (c3) performing steps (d) and (e).

* * * * *